(12) United States Patent
Campbell et al.

(10) Patent No.: US 11,273,199 B2
(45) Date of Patent: Mar. 15, 2022

(54) TREATMENT OF AGE-RELATED MACULAR DEGENERATION

(71) Applicant: THE PROVOST, FELLOWS, FOUNDATION SCHOLARS & THE OTHER MEMBERS OF BOARD, OF THE COLLEGE OF THE HOLY & UNDIV. TRINITY OF QUEEN EL, Dublin (IE)

(72) Inventors: Matthew Campbell, Dublin (IE); Sarah Doyle, Dublin (IE); Natalie Hudson, Dublin (IE); Lucia Clekova, Dublin (IE)

(73) Assignee: The Provost, Fellows, Foundation Scholars & The Other Members Of Board, of he College of the Holy & Undiv. Trinity of Queen El, Dublin (IE)

( * ) Notice: Subject to any disclaimer, the term of this patent is extended or adjusted under 35 U.S.C. 154(b) by 0 days.

(21) Appl. No.: 16/335,441

(22) PCT Filed: Sep. 22, 2017

(86) PCT No.: PCT/EP2017/074053
§ 371 (c)(1),
(2) Date: Mar. 21, 2019

(87) PCT Pub. No.: WO2018/055094
PCT Pub. Date: Mar. 29, 2018

(65) Prior Publication Data
US 2020/0016236 A1 Jan. 16, 2020

(30) Foreign Application Priority Data
Sep. 22, 2016 (GB) .................................... 1616158

(51) Int. Cl.
*A61K 38/17* (2006.01)
*A61K 9/00* (2006.01)

(52) U.S. Cl.
CPC ........ *A61K 38/1709* (2013.01); *A61K 9/0048* (2013.01)

(58) Field of Classification Search
None
See application file for complete search history.

(56) References Cited

U.S. PATENT DOCUMENTS

2012/0156202 A1 6/2012 Shantha et al.

FOREIGN PATENT DOCUMENTS

EP 2163548 A1 3/2010

OTHER PUBLICATIONS

Anonymous "Macular Degeneration Treatments" American Macular Degeneration Foundation, https://www.macular.org/treatments. (Year: 2016).*
Dunaief J "Prevention of Age-Related Macular Degeneration" Bright Focus Foundation. https://www.brightfocus.org/macular/article/prevention-age-related-macular. (Year: 2016).*
Campbell et al. "An experimental platform for systemic drug delivery to the retina" Proc. Natl. Acad. Sci. 106:17817-17822. (Year: 2009).*
International Search Report dated Nov. 30, 2017.
Maria Luisa Fanjul-Moles et al., "Relationship between Oxidative Stress, Circadian Rhythms, and AMD", Oxidative Medicine and Cellular Longevity, vol. 2016, Dec. 28, 2015, pp. 1-18.
Shaomin Peng et al., "Effects of Proinflammatory Cytokines on the Claudin-19 Rich Tight Junctions of Human Retinal Pigment Epithelium", Investigative Opthalmology & Visual Science, vol. 53., No. 8, Jul. 27, 2012, pp. 5016-5028.

* cited by examiner

*Primary Examiner* — Sudhakar Katakam
*Assistant Examiner* — Zachary J Miknis
(74) *Attorney, Agent, or Firm* — Miles & Stockbridge P.C.; Ajay A. Jagtiani

(57) ABSTRACT

The present invention relates to a method and compositions for the treatment of age-related macular degeneration (AMD), in particular dry-AMD, specifically geographic atrophy (GA) or advanced dry-AMD. Specifically, the invention relates to an inner-blood-retinal-barrier (iBRB) or blood-brain-barrier (BBB) tight junction protein and/or a circadian clock protein for use in the prevention and/or treatment of age-related macular degeneration.

15 Claims, 13 Drawing Sheets
Specification includes a Sequence Listing.

A
129

B
CD1

TREATMENT OF AGE-RELATED MACULAR DEGENERATION

FIELD OF THE INVENTION

The present invention relates to a method and compositions for the treatment of age-related macular degeneration (AMD), in particular dry-AMD, specifically geographic atrophy (GA) or advanced dry-AMD.

BACKGROUND OF THE INVENTION

Globally, an estimated 161 million people are visually handicapped, among which 37 million fall within the category of legal blindness, generally accepted to have visual acuity of <3/60 or corresponding visual field loss to <10 degrees. The most common causes of visual handicap are cataract and glaucoma. However, in the developed world, age-related macular degeneration (AMD) is the most prevalent cause of registered blindness in the older population, closely followed by diabetic retinopathy.

Epidemiological studies of AMD have been undertaken in at least nine countries. In one study from the United States (US), 1.75 million people were estimated to have advanced AMD defined as geographic atrophy (GA) or neovascularisation in at least one eye, with 7.3 million people at risk of developing the disease owing to the presence of drusen, tiny yellow or white accumulations of extracellular material that build up between Bruch's membrane and the retinal pigment epithelium of the eye. In another study from the United Kingdom (UK), it was found that there are currently 172,000 and 245,000 people with GA and neovascular AMD respectively, while a study from Germany found that there are 710,000 cases of advanced AMD, predicted to increase to over one million by 2020. Given that, in the overall, only limited therapies are available for these diseases, their negative social and economic impact is immense. The cost of AMD, involving diagnosis, monitoring, visual aids, habitation, accident treatment, rehabilitation, treatment of associated depression and anxiety, as well as direct treatment of the disease itself has been estimated to amount to approximately €200,000 per patient in any five year period.

AMD is the leading cause of central retinal vision loss worldwide. Drusen accumulation is the major pathological hallmark common to both dry and wet AMD. While numerous mechanisms have been proposed and some implicated in disease progression; to date, the pathways leading to the end stage of the condition remain unclear. It is estimated that 1 in 10 people over the age of 55 show early signs of AMD. In 10% of patients with AMD, blood vessels sprout from underlying choroidal vasculature disrupting retinal tissue integrity, leading to vision loss. Although less common, the neovascular form of the disease, termed "wet" AMD, is the most severe form and is termed a priority eye disease by the World Health Organization (WHO).

The major early pathological hallmark common to both dry and wet AMD is the accumulation of drusen behind the retina between the RPE and the choroid. Drusen is composed of extracellular components including, but not limited to, amyloid-$\beta$, vitronectin, cholesterols and almost every complement component. These components have all previously been identified in several tissues including blood and photoreceptors, and it is abundantly obvious that AMD is primarily a condition that involves aberrant clearance mechanisms. What is less clear however is the source of drusen and the dynamic events that occur during and after the diurnal shedding of photoreceptor outer segments and subsequent phagocytosis by the retinal pigment epithelium (RPE). On a daily basis, RPE cells phagocytose photoreceptor outer segments (POS) that are shed during renewal of photoreceptors. While some of the phagocytosed material is recycled to replenish essential components of the photoreceptors, other components in the material are exocytosed to the basolateral compartment of the RPE and are likely cleared by the systemic immune system. This is a highly regulated process controlled by autophagic processes and dysfunctional rates of clearance are likely a significant contributing factor to drusen accumulation in some individuals as evidenced by residual body build up in lysosomes observed in the RPE of AMD donor eyes.

While drusen deposition and localisation can differ from individual to individual, it is pertinent to consider that there is a considerable degree of symmetry in drusen patterning in each eye of a single individual. This correlates with an equally high degree of interocular symmetry of retinal blood vessels between right and left eyes. These blood vessels which form the inner blood-retina barrier (iBRB) are critical to maintaining retinal homeostasis. Endothelial cells that line these vessels have evolved tight junctions, a series of up to 30 interacting proteins that limit the paracellular space between endothelial cells to all but the smallest of molecules. As well as regulating the exchange of ions and macromolecules between the blood and the delicate neural microenvironment, these highly specialized endothelial cells protect the retina by restricting the entry of potentially damaging blood-borne agents such as neurotoxic chemicals, antibodies, pathogens, immune cells and anaphylatoxins. They also express a variety of transporters to control both the selective transport of nutrients into the retina and the efflux of metabolites and toxins from the retina via the transcellular pathway.

The end stage of "dry" AMD is termed geographic atrophy (GA), where the RPE begins to degenerate in the region of the macula and can eventually lead to death of cone photoreceptor cells and eventually central retinal vision loss. GA is primarily a disorder of a cell type at the back of the eye called the retinal pigment epithelium (RPE) and the present invention can regulate the flux of material into and out of the RPE, thereby relieving the stress exerted on this cell and preventing ultimate cell death. Given the pervasive nature of AMD in the developed world and the wealth of research in this area, the underlying molecular pathology associated with GA development is still far from clear. There are currently no therapies on the market to prevent or slow the course of development of this form of blindness other than recommended lifestyle changes such as smoking cessation and dietary modification. Supplementation in the diet with multi-vitamins enriched with the anti-oxidants lutein and xeaxanthin have been reported to increase macular pigment which may be beneficial to patients with dry AMD.

In 2006, the FDA approved the use of Genentech's drug Lucentis® for use in the exudative form of AMD where choroidal neovascularisation (CNV) is the hallmark pathology. While Lucentis® is indicated for use in the treatment of wet AMD, a highly similar drug, also originally manufactured by Genentech, Avastin®, is used "off-label" for the treatment of wet AMD. Recently, Regeneron Pharmaceuticals, Inc. released Eylea®, which is a fusion protein that acts as a decoy receptor for the vascular endothelial growth factor receptor 2 (VEGFR2). However, these drugs are prohibitively expensive with Lucentis® and Eylea®, having a cost of approximately €1,200-€1,500 per injection, while Avastin® costs approximately €110 per injection.

Thus, there remains a need to develop alternative therapies for AMD, both wet and dry AMD.

The mammalian circadian clock in the neurons of suprachiasmatic nuclei (SCN) in the brain and in cells of peripheral tissues is driven by a self-sustained molecular oscillator, which generates rhythmic gene expression with a periodicity of about 24 hours. The 24-hour circadian cycle is controlled by the oscillatory expression of a clock gene cassette including Period (Per) 1-3, Cryptochrome (Cry) 1/2, Clock, and Bmal1/2.

Circadian clocks influence nearly all aspects of physiology and behaviour, including rest-wake cycle, cardiovascular activity, hormone secretion, body temperature, and metabolism. Circadian rhythms are conserved across species even in nocturnal animals. All of the circadian clock components cycle identically in every species from Drosophila through mouse to man. While up to 40% of genes can cycle in a circadian fashion, very few genes display this characteristic cycling in all tissue with the same rhythm. Intriguingly, if one clock component is out of synchronisation, the entire system is at risk of failing which can lead to a wide and varied amount of phenotypes in mammalian systems. For example, Bmal knockout mice have a range of phenotypes including decrease life span, low fertility, low body weight, age-dependent arthropathy, and brain astrogliosis.

SUMMARY OF THE INVENTION

According to a first aspect of the present invention, there is provided an inner-blood-retinal-barrier (iBRB) or blood-brain-barrier (BBB) tight junction protein and/or a circadian clock protein for use in the prevention and/or treatment of age-related macular degeneration.

Optionally, there is provided an inner-blood-retinal-barrier (iBRB) or blood-brain-barrier (BBB) tight junction protein for use in the prevention and/or treatment of age-related macular degeneration.

Optionally or additionally, there is provided a circadian clock protein for use in the prevention and/or treatment of age-related macular degeneration.

Optionally, there is provided an inner-blood-retinal-barrier (iBRB) or blood-brain-barrier (BBB) tight junction protein and a circadian clock protein for use in the prevention and/or treatment of age-related macular degeneration.

According to a second aspect of the present invention, there is provided a method for the prevention and/or treatment of age-related macular degeneration in a subject, the method comprising the step of administering an inner-blood-retinal-barrier (iBRB) or blood-brain-barrier (BBB) tight junction protein and/or a circadian clock protein to the subject.

Optionally, the method comprises the step of administering an inner-blood-retinal-barrier (iBRB) or blood-brain-barrier (BBB) tight junction protein to the subject.

Optionally or additionally, the method comprises the step of administering a circadian clock protein to the subject.

Optionally, the method comprises the step of administering an inner-blood-retinal-barrier (iBRB) or blood-brain-barrier (BBB) tight junction protein and a circadian clock protein to the subject.

According to a third aspect of the present invention, there is provided use of an inner-blood-retinal-barrier (iBRB) or blood-brain-barrier (BBB) tight junction protein and/or a circadian clock protein in the manufacture of a medicament for the prevention and/or treatment of age-related macular degeneration.

Optionally, there is provided use of an inner-blood-retinal-barrier (iBRB) or blood-brain-barrier (BBB) tight junction protein in the manufacture of a medicament for the prevention and/or treatment of age-related macular degeneration.

Optionally or additionally, there is provided use of a circadian clock protein in the manufacture of a medicament for the prevention and/or treatment of age-related macular degeneration.

Optionally, there is provided use of an inner-blood-retinal-barrier (iBRB) or blood-brain-barrier (BBB) tight junction protein and a circadian clock protein in the manufacture of a medicament for the prevention and/or treatment of age-related macular degeneration.

According to a fourth aspect of the present invention, there is provided an expression vector comprising a nucleic acid sequence encoding an inner-blood-retinal-barrier (iBRB) or blood-brain-barrier (BBB) tight junction protein and/or a nucleic acid sequence encoding a circadian clock protein for use in the prevention and/or treatment of age-related macular degeneration.

According to a fifth aspect of the present invention, there is provided a composition comprising an inner-blood-retinal-barrier (iBRB) or blood-brain-barrier (BBB) tight junction protein and/or a circadian clock protein for use in the prevention and/or treatment of age-related macular degeneration.

Optionally or additionally, the composition comprises an expression vector comprising a nucleic acid sequence encoding an inner-blood-retinal-barrier (iBRB) or blood-brain-barrier (BBB) tight junction protein and/or a nucleic acid sequence encoding a circadian clock protein.

Optionally, the composition comprises an inner-blood-retinal-barrier (iBRB) or blood-brain-barrier (BBB) tight junction protein and/or a circadian clock protein; and an expression vector comprising a nucleic acid sequence encoding an inner-blood-retinal-barrier (iBRB) or blood-brain-barrier (BBB) tight junction protein and/or a nucleic acid sequence encoding a circadian clock protein.

Optionally, the use or administration restores the natural circadian cycling of the proteins in the iBRB.

Further optionally, the use or administration restores the natural circadian cycling of the proteins in the iBRB over a period of less than 24 hours.

Alternatively, the use or administration restores the natural circadian cycling of the proteins in the iBRB over a period of 24 hours.

Further alternatively, the use or administration restores the natural circadian cycling of the proteins in the iBRB over a period of more than 24 hours.

Optionally, the use or administration comprises increasing the amount of the inner-blood-retinal-barrier (iBRB) or blood-brain-barrier (BBB) tight junction protein over a period of less than 24 hours, 24 hours, or more than 24 hours.

Optionally or additionally, the use or administration comprises decreasing the amount of the inner-blood-retinal-barrier (iBRB) or blood-brain-barrier (BBB) tight junction protein over a period of less than 24 hours, 24 hours, or more than 24 hours.

Optionally, the use or administration comprises sequentially increasing and decreasing the amount of the inner-blood-retinal-barrier (iBRB) or blood-brain-barrier (BBB) tight junction protein over a period of less than 24 hours, 24 hours, or more than 24 hours.

Optionally or additionally, the use or administration comprises increasing the amount of the circadian clock protein over a period of less than 24 hours, 24 hours, or more than 24 hours.

Optionally or additionally, the use or administration comprises decreasing the amount of the circadian clock protein over a period of less than 24 hours, 24 hours, or more than 24 hours.

Optionally, the use or administration comprises sequentially increasing and decreasing the amount of the circadian clock protein over a period of less than 24 hours, 24 hours, or more than 24 hours.

Optionally, the use or administration comprises increasing the expression of a nucleic acid encoding the inner-blood-retinal-barrier (iBRB) or blood-brain-barrier (BBB) tight junction protein over a period of less than 24 hours, 24 hours, or more than 24 hours.

Optionally or additionally, the use or administration comprises decreasing the expression of a nucleic acid encoding the inner-blood-retinal-barrier (iBRB) or blood-brain-barrier (BBB) tight junction protein over a period of less than 24 hours, 24 hours, or more than 24 hours.

Optionally, the use or administration comprises sequentially increasing and decreasing the expression of a nucleic acid encoding the inner-blood-retinal-barrier (iBRB) or blood-brain-barrier (BBB) tight junction protein over a period of less than 24 hours, 24 hours, or more than 24 hours.

Optionally or additionally, the use or administration comprises increasing the expression of a nucleic acid encoding the circadian clock protein over a period of less than 24 hours, 24 hours, or more than 24 hours.

Optionally or additionally, the use or administration comprises decreasing the expression of a nucleic acid encoding the circadian clock protein over a period of less than 24 hours, 24 hours, or more than 24 hours.

Optionally, the use or administration comprises sequentially increasing and decreasing the expression of a nucleic acid encoding the circadian clock protein over a period of less than 24 hours, 24 hours, or more than 24 hours.

Optionally, the use or administration comprises increasing the amount of the inner-blood-retinal-barrier (iBRB) or blood-brain-barrier (BBB) tight junction protein over a first period of less than 12 hours, 12 hours, or more than 12 hours.

Optionally or additionally, the use or administration comprises decreasing the amount of the inner-blood-retinal-barrier (iBRB) or blood-brain-barrier (BBB) tight junction protein over a second period of less than 12 hours, 12 hours, or more than 12 hours.

Optionally, the use or administration comprises sequentially increasing the amount of the inner-blood-retinal-barrier (iBRB) or blood-brain-barrier (BBB) tight junction protein over a first period of less than 12 hours, 12 hours, or more than 12 hours; and decreasing the amount of the inner-blood-retinal-barrier (iBRB) or blood-brain-barrier (BBB) tight junction protein over a second period of less than 12 hours, 12 hours, or more than 12 hours.

Optionally or additionally, the use or administration comprises increasing the amount of the circadian clock protein over a first period of less than 12 hours, 12 hours, or more than 12 hours.

Optionally or additionally, the use or administration comprises decreasing the amount of the circadian clock protein over a first period of less than 12 hours, 12 hours, or more than 12 hours.

Optionally, the use or administration comprises sequentially increasing the amount of the circadian clock protein over a first period of less than 12 hours, 12 hours, or more than 12 hours; and decreasing the amount of the circadian clock protein over a second period of less than 12 hours, 12 hours, or more than 12 hours.

Optionally, the use or administration comprises increasing the expression of a nucleic acid encoding the inner-blood-retinal-barrier (iBRB) or blood-brain-barrier (BBB) tight junction protein over a first period of less than 12 hours, 12 hours, or more than 12 hours.

Optionally or additionally, the use or administration comprises decreasing the expression of a nucleic acid encoding the inner-blood-retinal-barrier (iBRB) or blood-brain-barrier (BBB) tight junction protein over a second period of less than 12 hours, 12 hours, or more than 12 hours.

Optionally, the use or administration comprises sequentially increasing the expression of a nucleic acid encoding the inner-blood-retinal-barrier (iBRB) or blood-brain-barrier (BBB) tight junction protein over a first period of less than 12 hours, 12 hours, or more than 12 hours; and decreasing the expression of a nucleic acid encoding the inner-blood-retinal-barrier (iBRB) or blood-brain-barrier (BBB) tight junction protein over a second period of less than 12 hours, 12 hours, or more than 12 hours.

Optionally or additionally, the use or administration comprises increasing the expression of a nucleic acid encoding the circadian clock protein over a first period of less than 12 hours, 12 hours, or more than 12 hours.

Optionally or additionally, the use or administration comprises decreasing the expression of a nucleic acid encoding the circadian clock protein over a second period of less than 12 hours, 12 hours, or more than 12 hours.

Optionally, the use or administration comprises sequentially increasing the expression of a nucleic acid encoding the circadian clock protein over a first period of less than 12 hours, 12 hours, or more than 12 hours; and decreasing the expression of a nucleic acid encoding the circadian clock protein over a second period of less than 12 hours, 12 hours, or more than 12 hours.

Optionally, the use or administration comprises increasing or decreasing the amount of the inner-blood-retinal-barrier (iBRB) or blood-brain-barrier (BBB) tight junction protein or the expression of the nucleic acid encoding the inner-blood-retinal-barrier (iBRB) or blood-brain-barrier (BBB) tight junction protein relative to a normal control.

Optionally or additionally, the use or administration comprises increasing or decreasing the amount of the circadian clock protein or the expression of the nucleic acid encoding the circadian clock protein relative to a normal control.

Optionally, the use or administration comprises increasing or decreasing the amount of the inner-blood-retinal-barrier (iBRB) or blood-brain-barrier (BBB) tight junction protein and the circadian clock protein; or increasing or decreasing the expression of the nucleic acid encoding the inner-blood-retinal-barrier (iBRB) or blood-brain-barrier (BBB) tight junction protein and the circadian clock protein; each relative to a normal control.

Optionally, a normal control is an amount of the inner-blood-retinal-barrier (iBRB) or blood-brain-barrier (BBB) tight junction protein and/or the circadian clock protein in a healthy subject or a subject not suffering from age-related macular degeneration, dry-AMD, wet-AMD, and/or geographic atrophy (GA).

Optionally, a normal control is an amount of the expression of the nucleic acid encoding the inner-blood-retinal-barrier (iBRB) or blood-brain-barrier (BBB) tight junction protein and/or the expression of the nucleic acid encoding the circadian clock protein in a healthy subject or a subject not suffering from age-related macular degeneration, dry-AMD, wet-AMD, and/or geographic atrophy (GA).

Optionally, a normal control is an amount of the inner-blood-retinal-barrier (iBRB) or blood-brain-barrier (BBB) tight junction protein and/or the circadian clock protein in a preceding period of less than 12 hours, 12 hours, or more than 12 hours.

Optionally, a normal control is an amount of the expression of the nucleic acid encoding the inner-blood-retinal-barrier (iBRB) or blood-brain-barrier (BBB) tight junction protein and/or the expression of the nucleic acid encoding the circadian clock protein in a preceding period of less than 12 hours, 12 hours, or more than 12 hours.

Optionally, the use or administration comprises increasing or decreasing the amount of the inner-blood-retinal-barrier (iBRB) or blood-brain-barrier (BBB) tight junction protein and/or the circadian clock protein; or increasing or decreasing the expression of the nucleic acid encoding the inner-blood-retinal-barrier (iBRB) or blood-brain-barrier (BBB) tight junction protein and/or the circadian clock protein; each by up to 50% relative to a normal control.

Further optionally, the use or administration comprises increasing or decreasing the amount of the inner-blood-retinal-barrier (iBRB) or blood-brain-barrier (BBB) tight junction protein and/or the circadian clock protein; or increasing or decreasing the expression of the nucleic acid encoding the inner-blood-retinal-barrier (iBRB) or blood-brain-barrier (BBB) tight junction protein and/or the circadian clock protein; each by up to 50%, optionally up to 40%, optionally up to 30%, optionally up to 20%, optionally up to 10%, relative to a normal control.

Optionally, the use or administration comprises increasing or decreasing the amount of the inner-blood-retinal-barrier (iBRB) or blood-brain-barrier (BBB) tight junction protein and/or the circadian clock protein; or increasing or decreasing the expression of the nucleic acid encoding the inner-blood-retinal-barrier (iBRB) or blood-brain-barrier (BBB) tight junction protein and/or the circadian clock protein; each by more than 50% relative to a normal control.

Further optionally, the use or administration comprises increasing or decreasing the amount of the inner-blood-retinal-barrier (iBRB) or blood-brain-barrier (BBB) tight junction protein and/or the circadian clock protein; or increasing or decreasing the expression of the nucleic acid encoding the inner-blood-retinal-barrier (iBRB) or blood-brain-barrier (BBB) tight junction protein and/or the circadian clock protein; each by more than 50%, optionally more than 60%, optionally more than 70%, optionally more than 80%, optionally more than 90%, relative to a normal control.

Optionally, the inner-blood-retinal-barrier (iBRB) or blood-brain-barrier (BBB) tight junction protein and/or the circadian clock protein is for use in the prevention and/or treatment of dry-AMD.

Optionally, the inner-blood-retinal-barrier (iBRB) or blood-brain-barrier (BBB) tight junction protein and/or the circadian clock protein is for use in the prevention and/or treatment of wet-AMD.

Optionally, the inner-blood-retinal-barrier (iBRB) or blood-brain-barrier (BBB) tight junction protein and/or the circadian clock protein is for use in the prevention and/or treatment of geographic atrophy (GA).

Optionally, there is provided an inner blood retinal barrier (iBRB)/blood brain barrier (BBB) tight junction protein and/or a circadian clock protein that affects iBRB/BBB tight junction protein expression, for use in the prevention and/or treatment of age-related macular degeneration, wherein the treatment involves restoring the natural circadian cycling of the proteins in the iBRB over a 24 hour period. Preferably, the protein is for use in the treatment and/or prevention of dry-AMD, more preferably geographic atrophy.

Optionally, the inner-blood-retinal-barrier (iBRB) or blood-brain-barrier (BBB) tight junction protein is selected from the claudin family of proteins.

Further optionally, the inner-blood-retinal-barrier (iBRB) or blood-brain-barrier (BBB) tight junction protein is selected from a claudin-1, claudin-3, claudin-5, claudin-12 protein, and combinations each thereof.

Still further optionally, the inner-blood-retinal-barrier (iBRB) or blood-brain-barrier (BBB) tight junction protein is a claudin-5 protein.

Optionally or additionally, the inner-blood-retinal-barrier (iBRB) or blood-brain-barrier (BBB) tight junction protein is selected from occludin, tricellulin, Lipolysis-stimulated lipoprotein receptor (LSR), zonula occluden-1 (ZO-1), junctional adhesion molecule (JAM), and combinations each thereof.

Optionally, the inner-blood-retinal-barrier (iBRB) or blood-brain-barrier (BBB) tight junction protein is selected from claudin-1, claudin-3, claudin-5, claudin-12, occludin, tricellulin, Lipolysis-stimulated lipoprotein receptor (LSR), zonula occluden-1 (ZO-1), junctional adhesion molecule (JAM), and combinations each thereof.

Optionally, the circadian clock protein is selected from period-1 (Per-1), period-2 (Per-2), period-3 (Per-3), cryptochrome-1 (Cry-1), cryptochrome-2 (Cry-2), Clock, brain and muscle aryl hydrocarbon receptor nuclear translocator like-1 (BMAL-1), brain and muscle aryl hydrocarbon receptor nuclear translocator like-2 (BMAL-2), Rev-ErbA alpha (NR1D1), and combinations each thereof.

Optionally, the circadian clock protein is selected from period-2 (Per-2), brain and muscle aryl hydrocarbon receptor nuclear translocator like-1 (BMAL-1), Rev-ErbA alpha (NR1D1), and combinations each thereof.

Optionally, there is provided a claudin-5 protein and/or a circadian clock protein that affects claudin-5 expression for use in the prevention and/or treatment of geographic atrophy (GA) associated with dry age-related macular degeneration (dry AMD), wherein the treatment involves restoring the natural circadian cycling of the proteins in the iBRB over a 24 hour period.

Optionally, there is provided an expression vector comprising a claudin-5 nucleic acid sequence or fragment thereof and/or a circadian clock nucleic acid sequence or fragment thereof that affects claudin-5 expression for use in the treatment of geographic atrophy (GA) associated with dry age-related macular degeneration (dry AMD), wherein the treatment involves restoring the natural circadian cycling of the proteins in the iBRB over a 24 hour period.

Optionally, there is provided a pharmaceutical composition comprising a claudin-5 protein or expression vector comprising a claudin-5 nucleic acid sequence or fragment thereof and/or a circadian clock protein that affects claudin-5 expression or expression vector a circadian clock nucleic acid sequence or fragment thereof that affects claudin-5 expression, for use in the prevention and/or treatment of associated with dry age-related macular degeneration (dry AMD), preferably geographic atrophy (GA), wherein the treatment involves restoring the natural circadian cycling of the proteins in the iBRB over a 24 hour period.

Optionally, there is provided a method for the prevention and/or treatment of age-related macular degeneration, wherein the treatment involves restoring the natural circadian cycling of the inner blood retinal barrier (iBRB) tight junction proteins, preferably claudin-5, and/or the circadian clock proteins that affects iBRB tight junction protein expression, preferably claudin-5, over a 24 hour period.

DETAILED DESCRIPTION OF THE INVENTION

In this specification, we have described the treatment in terms of restoring the natural circadian cycling of the proteins of interest in the iBRB and/or the BBB over a 24 hour period. The term 'natural cycling' or 'natural circadian cycling' is intended to be interchangeable with the terms 'dynamic cycling' or 'dynamic circadian cycling', 'circadian rhythm expression' and the like.

According to a general aspect of the invention, there is provided an inner blood retinal barrier (iBRB) tight junction protein and/or a circadian clock protein that affects iBRB tight junction protein expression, for use in the prevention and/or treatment of age-related macular degeneration, wherein the treatment involves restoring the natural circadian cycling of the proteins in the iBRB over a 24 hour period.

Preferably, the protein is for use in the treatment and/or prevention of dry AMD, more preferably geographic atrophy.

This general aspect of the invention is based on the findings that claudin-5, one of the inner blood retinal barrier (iBRB) tight junction proteins, surprisingly cycles at the BBB/iBRB. We have surprisingly demonstrated that the expression of claudin-5 is affected by circadian clock proteins that affect iBRB tight junction protein expression. These finding are entirely unexpected, as to date the iBRB and BBB are accepted as "static" environments. We have also shown there is a phenotypic correlation to this cycling (see FIGS. 10 and 11) and that persistent suppression of claudin-5 induces a GA phenotype.

Based on these findings, the invention is directed to the re-establishment of inner blood retinal barrier (iBRB) tight junction protein "cycling" and/or a circadian clock protein that affects iBRB tight junction protein "cycling" to treat AMD, particular dry-AMD, end stage dry AMD/GA.

The treatment involves restoring the circadian rhythm and/or resynchronizing the biological clock of the iBRB. The inventors have surprisingly found that re-establishing or restoring the natural cycling of the proteins of interest, particularly claudin-5, at the iBRB will regulate the passive diffusion of material into the photoreceptor outer segments and prevent the development of AMD, particularly late-stage AMD, geographic atrophy (GA).

Thus, the general aim is to maintain the inner blood retinal barrier (iBRB) tight junction protein and/or a circadian clock protein expression levels at normal levels over a 24 hour period and due to the cycling of these proteins, the method essentially aims to mimic, reinstate or restore the natural cycling/circadian rhythm expression of these proteins. Thus, the treatment covers the restoration or re-establishment of the natural or dynamic cycling of the proteins of interest where evening/night-time levels (from approximately 8 pm to 8 am) of the proteins of interest, particularly claudin-5 are decreased compared to morning/daytime levels.

In this manner, the levels of the proteins of interest, particularly claudin-5, can be upregulated and/or downregulated over a 24 hour period in order to restore the natural circadian rhythm of the iBRB and expression of the proteins of interest.

According to an aspect of the invention, there is provided a claudin-5 protein and/or a circadian clock protein that affects claudin-5 expression for use in the prevention and/or treatment of geographic atrophy (GA) associated with dry age-related macular degeneration (dry AMD), wherein the treatment involves restoring the natural circadian cycling of the proteins in the iBRB over a 24 hour period.

The inner blood-retinal barrier (inner BRB/iBRB) is created by complex tight junctions of retinal capillary endothelial cells. Although this barrier prevents the free diffusion of substances between the circulating blood and the neural retina, the inner BRB efficiently supplies nutrients to the retina.

In this manner, the iBRB tight junction protein, such as claudin-5, is a component of the inner retinal vasculature and is proposed as a therapeutic target for GA treatment. This is in contrast to the known suggested approaches to treating GA which involve targeting the RPE directly. The present invention advantageously provides a method for the early stage intervention treatment of dry AMD.

It is postulated that regulating levels of claudin-5 at the iBRB confers control over the delivery and replenishment of the outer segments of photoreceptors and consequently control the burden of material consumed by the RPE on a daily basis. Accordingly, Claudin-5 is proposed as a preferred target as it is the main component of the iBRB tight junction complex. Other tight junction proteins present in the iBRB tight junction complex include Occludin, claudin-1, -3, -12, tricellulin, LSR, ZO-1, junctional adhesion molecule (JAM) and could be additional (single or combination) targets for the proposed therapy.

The mammalian circadian clock in the neurons of suprachiasmatic nuclei (SCN) in the brain and in cells of peripheral tissues is driven by a self-sustained molecular oscillator, which generates rhythmic gene expression with a periodicity of about 24. 24 hour circadian cycle controlled by the oscillatory expression of a clock gene cassette including Period (Per) 1-3, Cryptochrome (Cry) 1/2, Clock, and Bmal1/2. The preferred circadian clock proteins that affects iBRB tight junction protein expression include Period (Per) 1-3, Cryptochrome (Cry) 1/2, Clock, and Bmal1/2, preferably BMAI1, Rev-Erb-alpha and/or Per2.

According to a preferred embodiment of the invention, there is provided a claudin-5 protein and/or a circadian clock protein that affects claudin-5 expression for use in the prevention and/or treatment of geographic atrophy (GA) associated with dry age-related macular degeneration (dry AMD), wherein the treatment involves restoring the natural circadian cycling of the claudin-5 protein in the iBRB over a 24 hour period.

It will be understood that the subject has a geographic atrophy phenotype or is a subject at risk of developing geographic atrophy, which can be based on current diagnostic methods, including determined area and size of drusen deposition that will lead to a diagnosis of dry AMD in the first instance.

In general terms, the treatment involves any means by which the natural circadian cycling of the proteins in the iBRB over a 24 hour period is restored and, for example, may take place by constitutively over-expressing the protein (or a vector comprising nucleic acid sequences) combined with the periodic suppression over a 24 hour period; or regulating the protein expression (or a vector comprising nucleic acid sequences) in a phased manner over a 24 hour period.

According to an aspect of the invention, there is provided an expression vector comprising claudin-5 nucleic acid sequences and/or a circadian clock nucleic acid sequences that affects claudin-5 expression for use in the treatment of geographic atrophy (GA) associated with dry age-related macular degeneration (dry AMD), wherein the treatment involves restoring the natural circadian cycling of the proteins in the iBRB over a 24 hour period.

Ideally, the nucleic acid is cDNA.

According to an aspect of the invention, there is provided a pharmaceutical composition comprising a claudin-5 protein or expression vector comprising claudin-5 nucleic acid sequences and/or a circadian clock protein that affects claudin-5 expression or expression vector comprising a circadian clock nucleic acid sequence that affects claudin-5 expression, for use in the prevention and/or treatment of geographic atrophy (GA) associated with dry age-related macular degeneration (dry AMD), wherein the treatment involves restoring the natural circadian cycling of the proteins in the iBRB over a 24 hour period.

According to all aspects and embodiments of the invention, the protein, expression vector, pharmaceutical composition may be provided in a form suitable for systemic, intravitreal or sub-retinal delivery.

In this manner, the treatment may be in the form of small molecules, recombinant proteins, antibodies, siRNAs or viral vectors.

It will be understood that the cycling of the inner blood retinal barrier (iBRB) tight junction protein, such as claudin-5, may be regulated directly.

Alternatively, the cycling of the inner blood retinal barrier (iBRB) tight junction protein, such as claudin-5, may be regulated indirectly by targeting circadian clock protein that affects iBRB tight junction protein expression. By targeting the circadian clock proteins, the downstream tight junction proteins can also be regulated.

Non-limiting and exemplary ways of direct and indirect targeting include:

a cDNA and/or shRNA based construct that will allow for constitutive over-expression of any one of claudin-5, BMAL-1, Reverb-alpha or Per2 while periodically allowing for its suppression using, for example, doxycycline inducible promoters driving claudin-5 shRNA or BMAL-1, or Reverb-alpha or Per2 shRNAs;

RNA interference (RNAi) agents, particularly siRNAs, can be delivered to the target cell exogenously or expressed endogenously in the form of short hairpin RNAs (shRNAs). In shRNA, the single RNA strand may form a hairpin structure with a stem and loop and, optionally, one or more unpaired portions at the 5' and/or 3' portion of the RNA;

periodic suppression is required as the method involves the constitutive over-expression of claudin-5 via cDNA based constructs. Periodic suppression of claudin-5 will restore the "cycling" of the protein again;

a regulatable claudin-5, BMAL-1, Reverb-alpha or Per2 cDNA expression vector that provides "phased" expression of the proteins;

ideally, the construct is doxycline regulatable. Other promoters and drugs may be used also. Ideally, this construct provides for phased daily exposure to doxycycline at the same time each day.

a pulsatile exposure to dexamethsone which can directly regulate claudin-5 or BMAL-1, or Reverb-alpha or Per2 levels in the eye;

ideally, this involves a slow release encapsulation device implanted into the eye or subcutaneously that will allow for a distinct amount of dexamethasone to be released daily at the same time. In this manner dexamethasone, which is know to regulate tight junctions, can be used in a pulsatile manner to phenocopy circadian cycling of claudin-5.

According an aspect of the invention, there is provided a method for the prevention and/or treatment of age-related macular degeneration, wherein the treatment involves restoring the natural circadian cycling of the inner blood retinal barrier (iBRB) tight junction proteins and/or the circadian clock protein that affects iBRB tight junction protein expression over a 24 hour period.

Ideally, the method is for the prevention and/or treatment of geographic atrophy (GA) associated with dry age-related macular degeneration (dry AMD).

According to a preferred embodiment, the method involves the regulation of inner blood retinal barrier (iBRB) tight junction protein, such as claudin-5, and/or the regulation of circadian clock protein that affects iBRB tight junction protein expression.

As defined above, the iBRB tight junction proteins can be selected from one or more of occludin, claudin-1, claudin-3, claudin-5, claudin-12, tricellulin, LSR, ZO-1 and/or junctional adhesion molecule (JAM).

As defined above, the circadian clock protein that affects iBRB tight junction protein expression can be selected from one or more of Period (Per) 1-3, Cryptochrome (Cry) 1/2, Clock, and Bmal1/2, preferably BMAI1, Rev-Erb-alpha and/or Per2.

According to a preferred embodiment, the protein is claudin-5 and/or a circadian clock protein that affects claudin-5 expression.

According to a more preferred embodiment, the method is the prevention and/or treatment of geographic atrophy (GA) associated with dry age-related macular degeneration (dry AMD). In this manner, the subject has a geographic atrophy phenotype or is at risk of developing GA based on determined area and size of drusen deposition.

BRIEF DESCRIPTION OF THE DRAWINGS

Embodiments of the invention will now be described with reference to the following non-limiting examples and drawings, in which.

EXAMPLES

Figure 1:
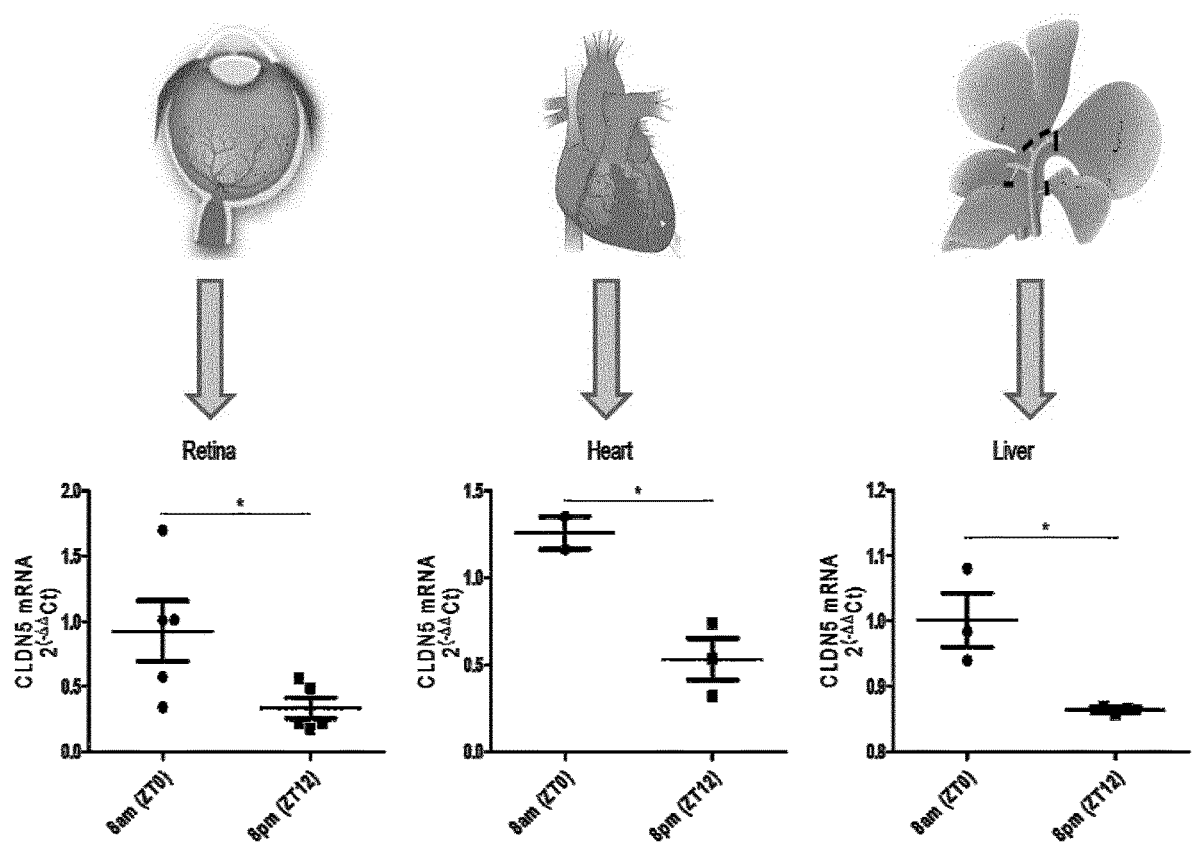
FIG. 1 illustrates retina, heart, and liver RNA isolated from 3-month old C57BL/6J mice at 8 and 8 pm, and transcript levels of claudin-5 analysed by SYBR green RT-PCR, wherein β-actin was used as a housekeeping gene reference for standardisation (*P<0.05)

Material & Methods
AAV Production
shRNAs designed to target transcripts derived from mouse claudin-5 were incorporated into AAV-2/9 vectors.

shRNA was cloned into the pSingle-tTS-shRNA (Clontech) vector in accordance with the manufacturer's instructions. The plasmid incorporating the inducible system with claudin-5 shRNA was digested with BsrBi and BsrGI and ligated into the Not1 site of the plasmid pAAV-MCS, such as to incorporate left and right AAV inverted terminal repeats (L-ITR and R-ITR). AAV-2/9 was then generated using a triple transfection system in a stably transfected HEK-293 cell line for the generation of high-titre viruses (Vector BioLabs).

Magnetic Resonance Imaging (MRI)

BRB integrity was assessed in vivo via MRI, using a dedicated small rodent 7 T MRI system located at TCD (www.neuroscience.tcd.ie/technologies/mri.php). Anaesthetised mice were physiologically monitored (ECG, respiration and temperature) and placed on an MRI-compatible support cradle, with a built-in system for maintaining the animal's body temperature at 37° C. The cradle was then positioned within the MRI scanner. Accurate positioning was ensured by acquiring an initial rapid pilot image, which was then used to ensure the correct geometry was scanned in all subsequent MRI experiments. Upon insertion into the MRI scanner, high resolution anatomical images of the brain were acquired (100 µm in-plane and 500 µm through-plane spatial resolution). To visualize brain damage and lesion volumes, high resolution images were acquired using Rapid Acquisition with Relaxation Enhancement (RARE) 2-D sequence with a RARE factor of 8 and an echo time resulting in an effective time of 42.2 ms (with a flip angle of 180°). With an acquisition matrix of 128×128 and a field of view of 1.8×1.8 $cm^2$, the pixel resolution was 0.141 mm/pixel. In the coronal plane, 15 slices, each measuring 0.25 mm in thickness were acquired. Repetition time was 7274.2 ms, and four averages were used for a total measuring time of 7 minutes 45 seconds.

Compromises of the BRB were then visualised in high resolution T1 weighted MR images (resolution, 0.156× 0.156×5 $mm^3$; field of view: 20×20×17.9 $mm^3$; matrix; 128×128×30; TR/TE: 500/2.7 ms; flip angle: 30°; number of averages: 3; acquisition time: 2 min, 24 sec; Repetitions: 12) following administration of 100 µl of a 1 in 3 dilution of Gd-DTPA (Gadolinium diethylene-triamine penta-acetic acid), administered via the tail vein.

Real-Time RT-PCR Analysis

Transcript levels were quantified using a two-step real-time reverse transcription polymerase chain reaction (RT-PCR) on the 7300 Real-Time PCR System (Applied Biosystems) with QuantiTect SYBR Green I (Qiagen) as a fluorescent dye. cDNA was reverse transcribed from RNA with the High-Capacity cDNA Reverse Transcription Kit (Applied Biosystems). Real-time PCR was performed with the FastStart Universal SYBR Green Master (ROX) master mix (Roche). The RT-PCR reaction conditions were as follows: 95° C.×10 min, (95° C.×10 s, 60° C.×30 s)×40, 95° C.×15 s, 60° C.×1 min, 95° C.×15 s, 60° C.×15 s. The primer sequences for the RT-PCR experiments were supplied by Sigma-Aldrich and were as follows: claudin-5 left, 5'-TTTCTTCTATGCGCAGTTGG-3', and right, 5'-GCAGTTTGGTGCCTACTTCA-3': β-actin left, 5'-TCACCCACACTGTGCCCATCTACGA-3' and right, 5'-CAGCGGAACCGCTCATTGCCAATGG-3'. Relative gene expression levels were measured using the comparative $C_T$ method ($\Delta\Delta C_T$). Expression levels of target genes were normalised to the housekeeping gene β-actin.

Cell Culture and Transfection

Mouse brain endothelial cells (Bend.3, American Type Culture Collection) were cultured in DMEM supplemented with 10% FCS and 2 mM sodium pyruvate in a 5% $CO_2$ incubator at 37° C. Bend.3 cells were seeded on 12 well plates (2.5*$10^5$ cells per well) and 100 ng/ml claudin-5 shRNA was transfected per well using Lipofectamine 2000. RNA was extracted from HEK293 cells and Bend.3 cells with the E.Z.N.A Total RNA Kit 1 (Omega biotek) according to the manufacturer's instructions. Proteins were isolated with lysis buffer (62.5 mM Tris, 2% SDS, 10 mM Dithiothreitol, 10 µl protease inhibitor cocktail/100 ml (Sigma Aldrich), followed by centrifugation at 12,000 RPM for 20 min@4° C. and supernatant was removed for claudin-5 protein analysis.

Fundus Fluorescein Angiography (FFA)

Mice were prepared for FFA analysis by instillation of tropicamide/phenylephrine eye drops and subsequently anaesthetised using Ketamine/Domitor mix. The fundus was imaged using a Heidelberg optical coherence tomography (OCT) machine and retinal vasculature was assessed following intra-peritoneal injection of a solution containing sodium fluorescein (2%). Images were acquired every 30 seconds for a period of 10 minutes.

Example 1

Claudin-5 is Regulated by the Circadian Clock

Figure 2:
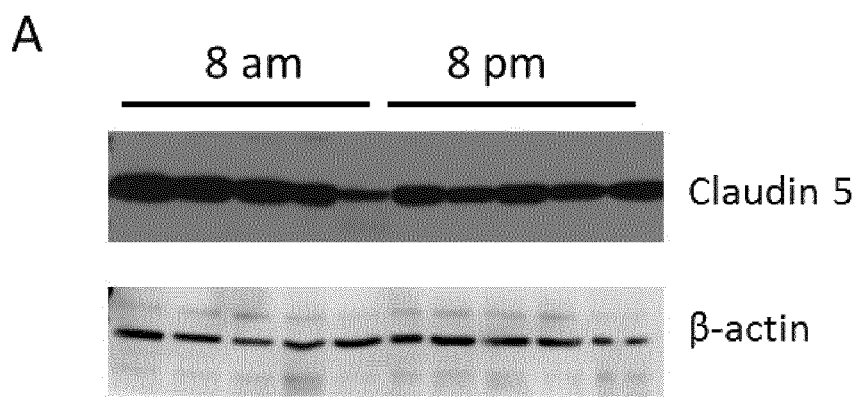
FIG. 2 illustrates a) retinae isolated from 3-month old C57BL/6J mice at 8 am and 8 pm that had been housed in normal light-dark conditions, wherein protein lysates were analysed by western blotting to determine the levels of claudin-5, with β-actin used as a loading control; b) densitometric quantification of claudin-5 expression showing a significant decrease at 8 pm relative to 8 am; c) exposure of mouse brain endothelial cells to 50% serum for 2 hours followed by serum-free media for the length of times indicated inducing claudin-5 cycling, wherein data are representative from 5 individual mice retinae and analysed by Student's t-test (*P value<0.05)
Figure 2:
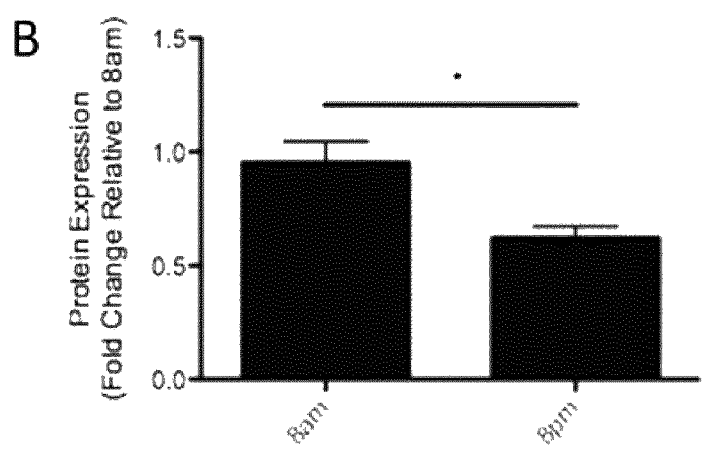
Figure 2:
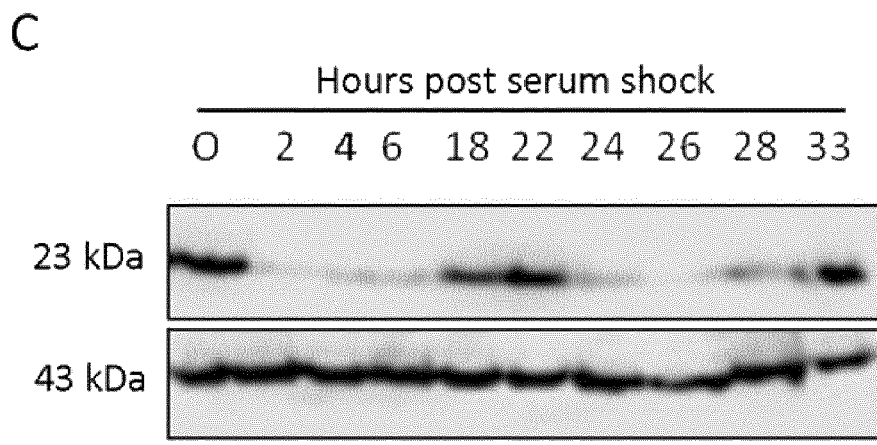
Figure 3:
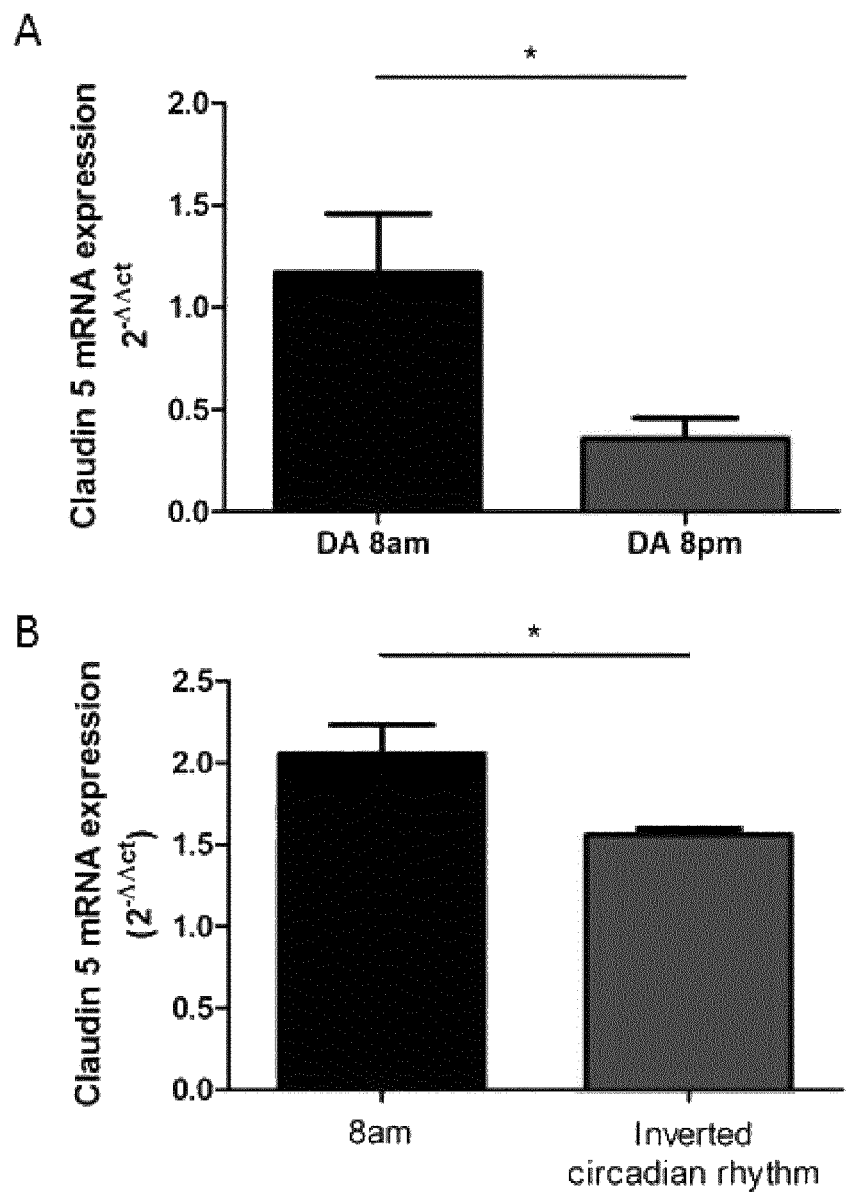
FIG. 3 illustrates a) retinae isolated from 3-month old C57BL/6J mice at 8 am and 8 pm that had been housed in 24 h darkness (DA) to see if the response was circadian or diurnal (i.e. due to light), and transcript levels of claudin-5 analysed by SYBR green RT-PCR, wherein β-actin was used as a house-keeping gene for standardisation; b) retinae isolated from 3-month old C57BL/6J mice that had their circadian rhythm inversed for 3 weeks (i.e. for these mice 8 am becomes 8 pm, 8 pm becomes 8 am) and compared to mice that had been kept on their normal light cycle, and claudin-5 transcript levels analysed as mentioned for a), wherein data are representative of retinae from 5 individual mice and analysed by Student's t-test (*P value<0.05)
Figure 4:
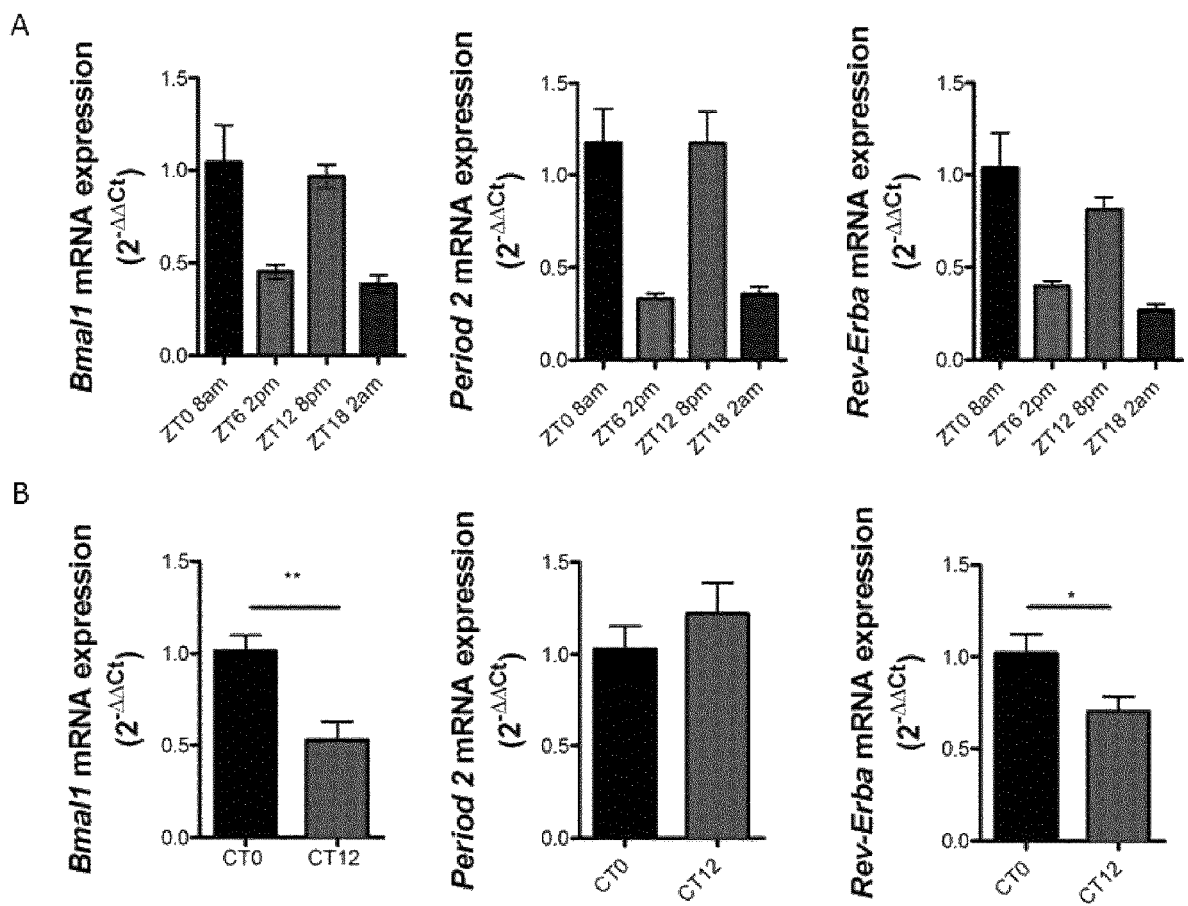
FIG. 4 illustrates a) retina RNA isolated from 3-month old C57BL/6J mice at 8 am and 8 pm and transcript expression for the clock components Bmal1, Period 2 and Rev-Erba analysed by SYBR green RT-PCR; b) transcript levels of Bmal1, Period 2, and Rev-Erba analysed from retinal RNA of mice that had been kept in 24 hours of darkness, wherein data are representative of retinae from 5 individual mice and analysed by Student's t-test (*P value<0.05, **P value<0.01)

Circadian rhythms are 24 hour oscillations in behaviour and physiology in response to environmental cues, primarily daylight and darkness. A conserved transcriptional-translational regulatory loop involving core clock components, gene protein products, are necessary for generation and regulation of circadian rhythms within individual cells. It was determined that claudin-5 was cycling in a circadian rhythm in all organs analysed (see FIG. 1). In tandem, claudin-5 protein levels are significantly decreased in the evening (8 PM) when compared to the morning (8 AM) in mice (see FIG. 2a, b). While in vitro, cells lose their circadian rhythm, following serum shock, it is possible to reset the circadian clock transiently. In primary mouse brain endothelial cells, serum shock induced cycling of claudin-5 in 12 hour phases similar to that observed in the retina and peripheral organs (see FIG. 2c). This response is circadian rather than diurnally regulated as claudin-5 levels remain lower in the evening compared to morning for mice that had been kept in 24 hours of darkness (see FIG. 3a). Circadian rhythms can be intrinsically inversed following 3 weeks of light alteration and we found that mice that have an inversed circadian rhythm, meaning 8 am is actually 8 pm, have lower claudin-5 levels (see FIG. 3b). Clock components BMAL1, Per2 and Rev-Erb-alpha were found to not cycle in an exact 24 hour cycle as expected (see FIG. 4a) although BMAL1 and Rev-Erb-alpha do have lower expression levels at 8 pm in mice that have been kept in darkness for 24 hours (see FIG. 4b).

Figure 5:
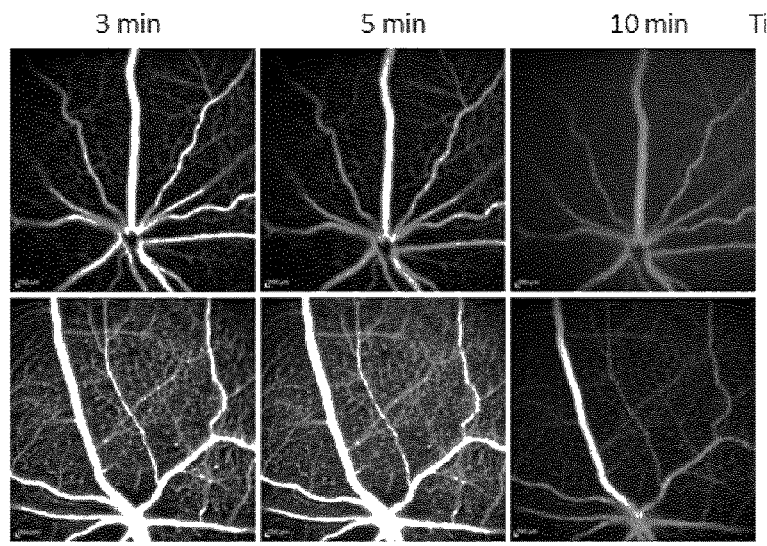
FIG. 5 illustrates fundus fluorescein angiography carried out at 8 am and 8 pm on C57BL/6J mice, wherein equal volume/weight of sodium fluorescein was injected per mouse, and two minutes post-injection images were taken every 30 seconds up to 10 minutes with the sensitivity of the images being kept the same at each time point, wherein the relative image density was analysed using Image J software and representative images at both 8 am and 8 pm are shown at 3, 5 and 10 min post injection, and wherein the top right hand graph shows the average image raw intensity density for the entire image across all images and time points, and the bottom right hand graph shows the area under the curve.
Figure 5:
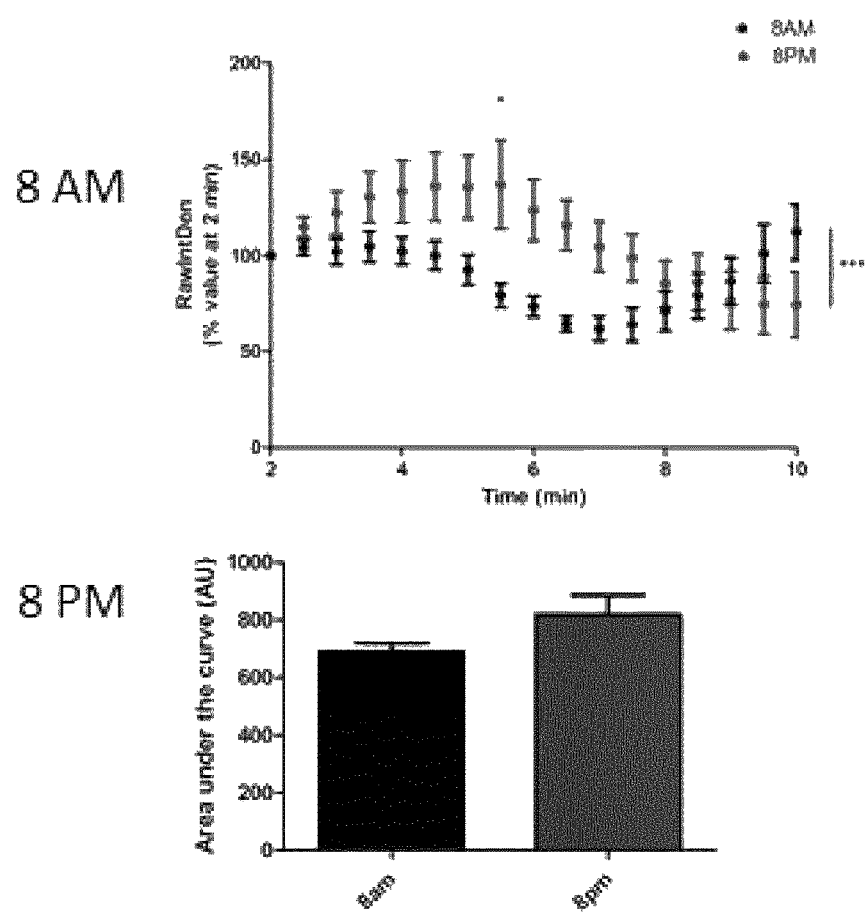
Figure 6:
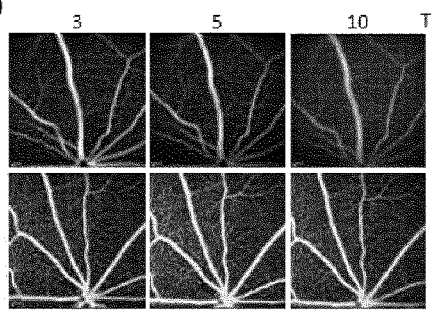
FIG. 6 illustrates fundus fluorescein angiography carried out at 8 am and 8 pm on a) 129 mice and b) CD1 mice in the same manner as described in FIG. 3, wherein representative images at both 8 am and 8 pm are shown at 3, 5 and 10 min post injection, and the graph to the right shows the average raw intensity density for microvessel permeability across all images and time points, wherein data are representative of at least 5 mice imaged at both time points and analysed by two-way ANOVA (*P value<0.05, P value<0.01, *P value<0.001)
Figure 6:
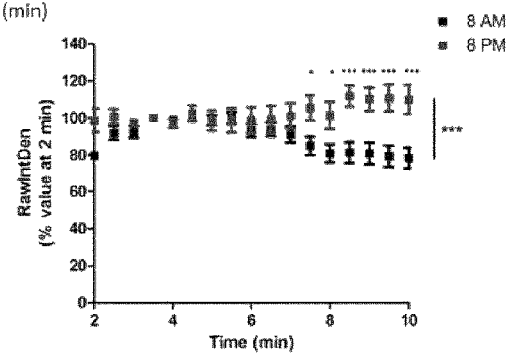
Figure 6:
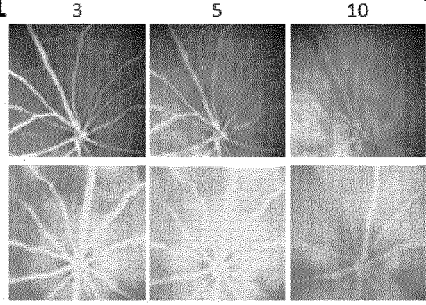
Figure 6:
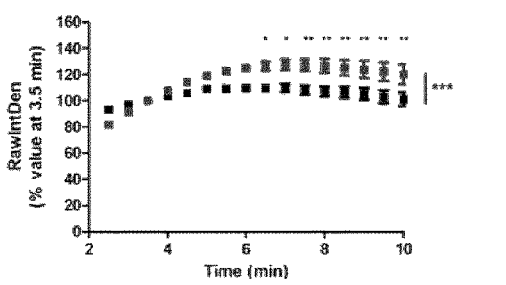
Figure 7:
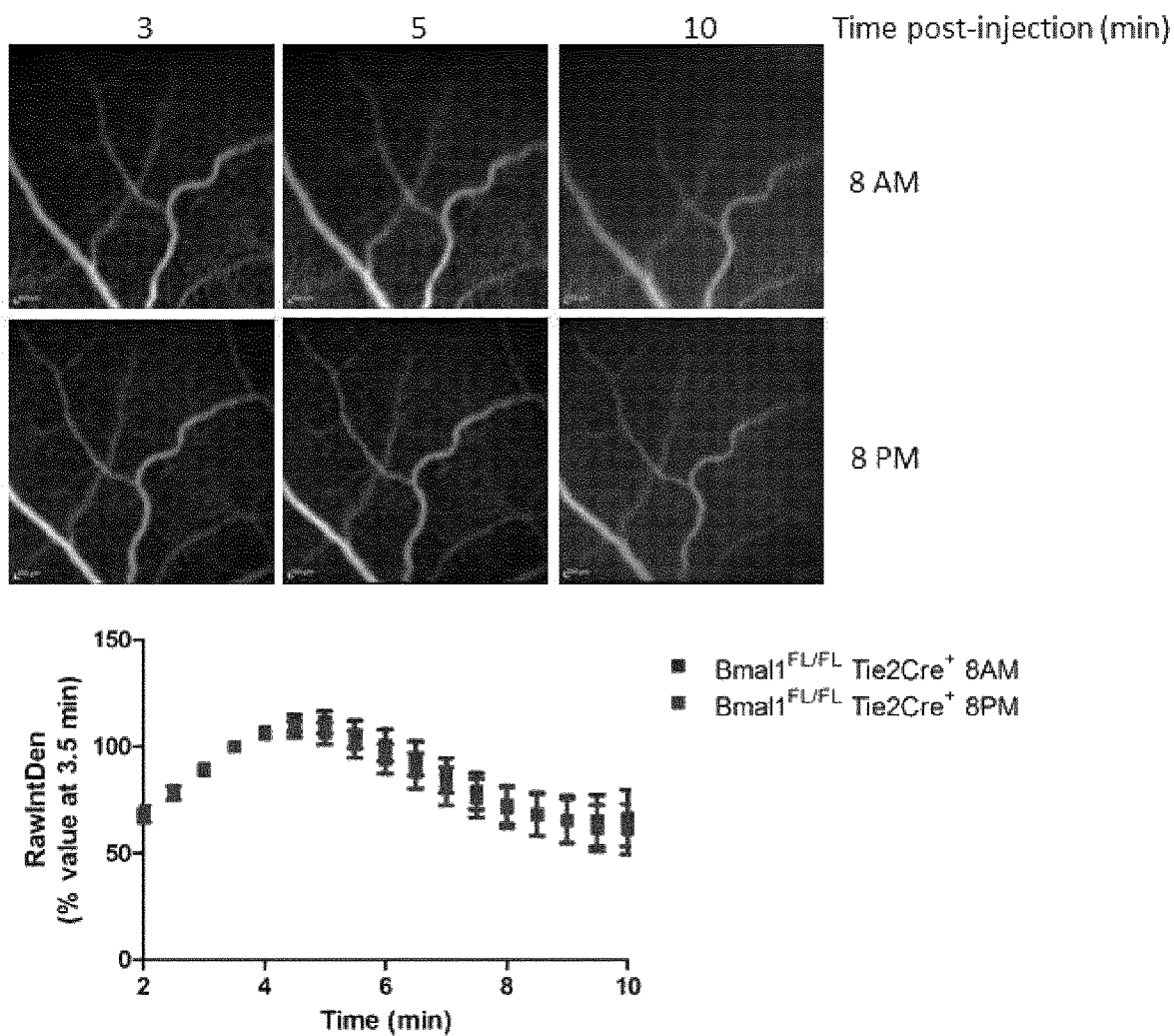
FIG. 7 illustrates BMAL1$^{FL/FL}$xTie2Cre$^+$ imaged at 8 am and 8 pm by fundus fluorescein angiography as previously described, wherein representative images from the same mouse imaged at both time points at 3, 5 and 10 min post-injection are shown, and the graph below shows microvessel permeability of all images across all time points, and there is no change in permeability between 8 am and 8 pm in mice lacking BMAL1 in their endothelial cells, wherein data are representative of 12 mice that were all imaged at both time points and analysed by two-way ANOVA (ns, P value>0.05)
Figure 8:
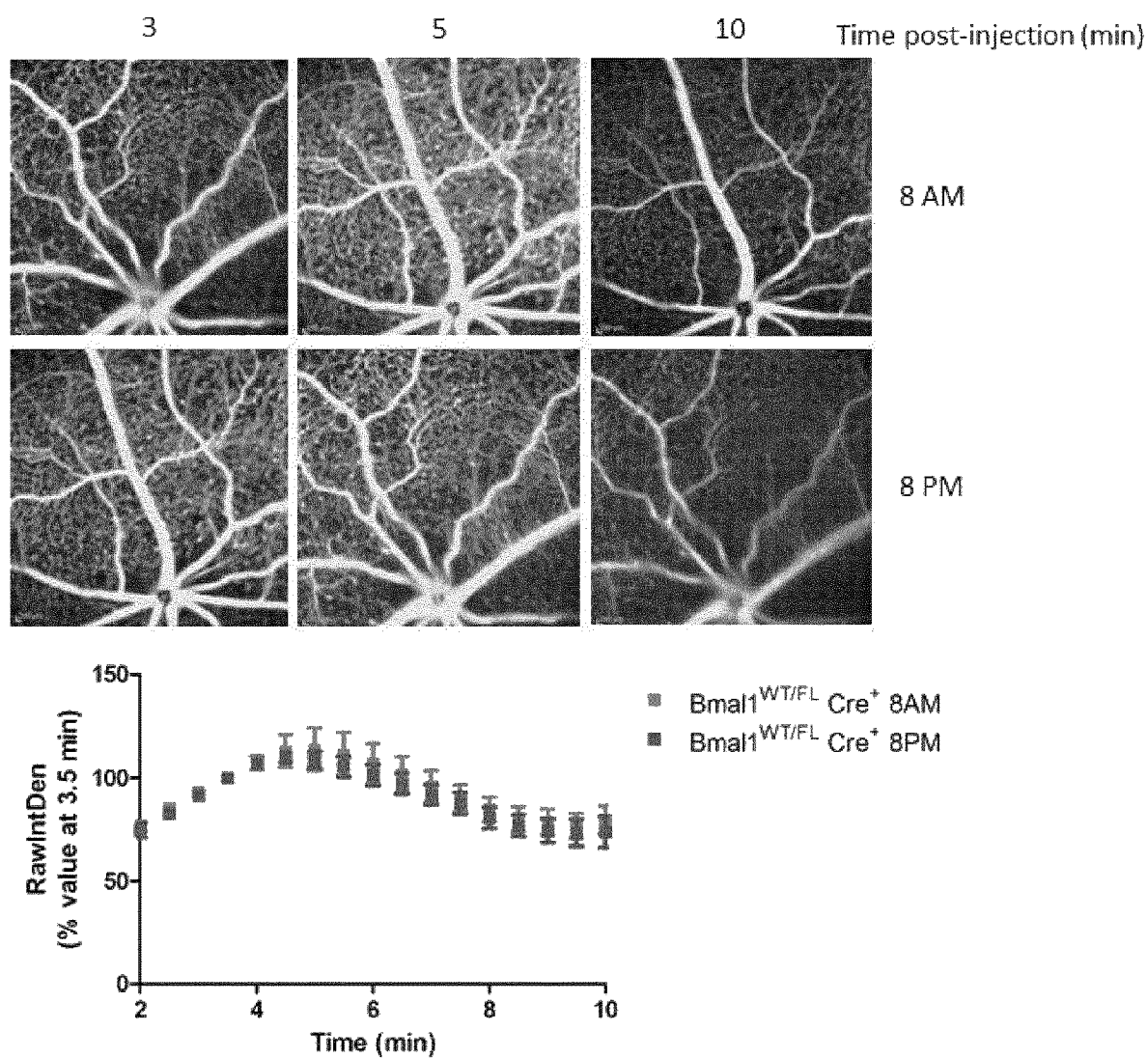
FIG. 8 illustrates BMAL1$^{WT/FL}$xTie2Cre$^+$ imaged at 8 am and 8 pm by fundus fluorescein angiography as previously described, wherein representative images from the same mouse imaged at both time points at 3, 5 and 10 min post-injection are shown, and the graph below shows that there is no change in permeability between 8 am and 8 pm in mice lacking just one copy of BMAL1 in their endothelial cells, wherein data are representative of 12 mice that were all imaged at both time points and analysed by two-way ANOVA (ns, P value>0.05)
Figure 9:
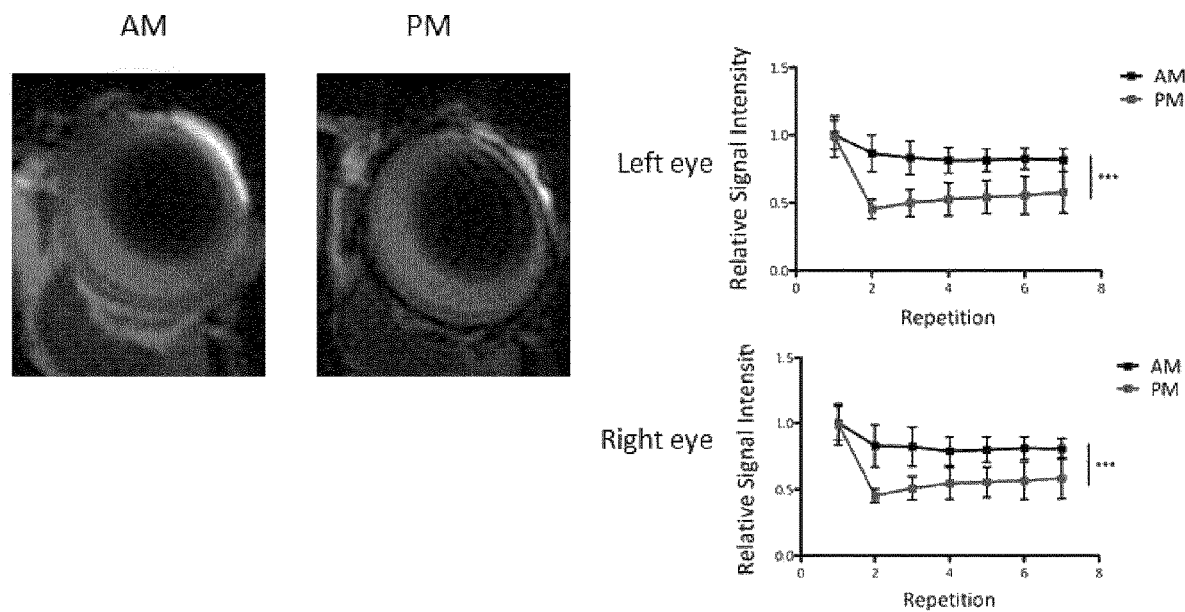
FIG. 9 illustrates inner blood-retinal barrier integrity in the morning and evening as studied by magnetic resonance imaging (MRI), wherein 3-month old C57BL/6J mice were injected via tail-vein with gadolinium diethylene-triamine penta-acetic acid (Gd-DTPA), and signal intensity for both the left and right eye were analysed, wherein data are representative of 5 mice and analysed by two-way ANOVA with Bonferroni post-hoc test (***P value<0.001)

Inner retinal blood vessels are more permeable in the evening compared to the morning. Given the changes in expression of the key tight junction component claudin-5 at various times of the day, retinal fundus fluoescein angiography (FFA) was performed at 8 AM compared to 8 PM. Retinal blood vessels appeared to be more "leaky" in the evening compared to the morning that correlated with the levels of claudin-5 protein expression at these time points (see FIG. 5). This phenomenon is not strain-specific as we also see 'leakier' vessels in the evening in both 129 mice and the CD1 strain (see FIG. 6a, b). Endothelial cell specific suppression of BMAL1, using BMAL1FL/FL mice crossed to Tie2Cre mice results in no changes in permeability at 8 am and 8 pm being observed (see FIG. 7). The loss of just one copy of BMAL1 appears to be sufficient in preventing the permeability changes seen (see FIG. 8). This is suggestive of BMAL1 playing a role in regulating retinal permeability changes. In corroboration, magnetic resonance imaging shows that the retina is more permissive in the evening (see FIG. 9).

Example 2

Figure 10:
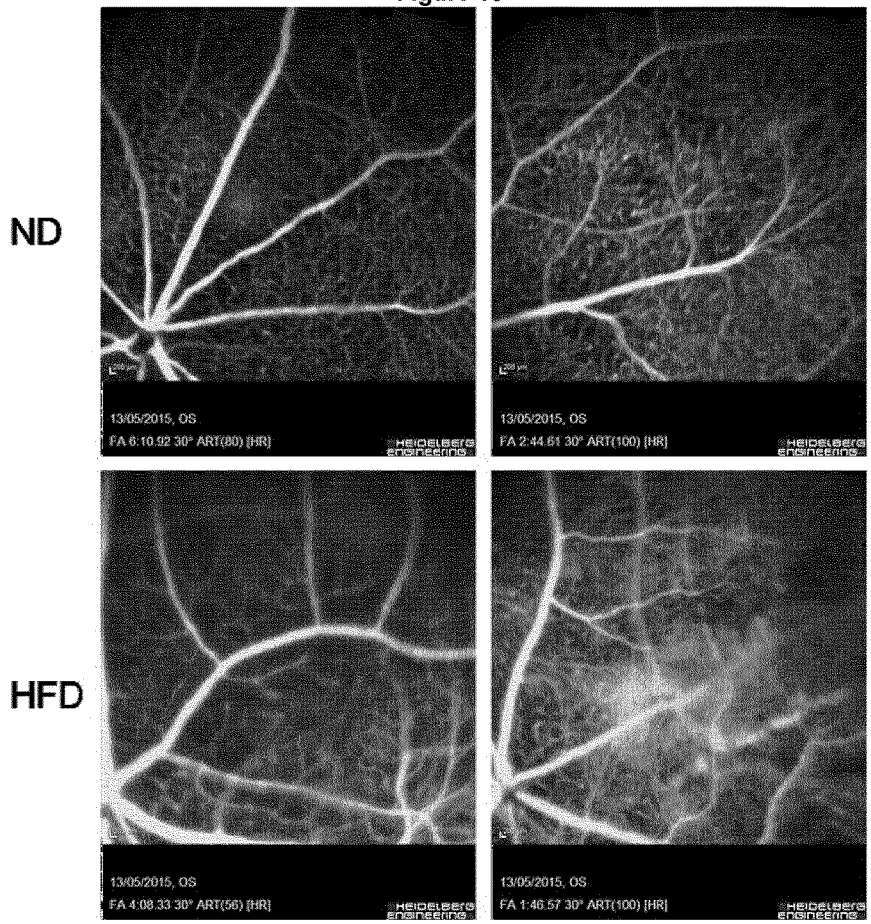
FIG. 10 illustrates NT AAV injected eye on normal diet (ND), top left panel; CL5 AAV injected eye on ND, top right panel; NT AAV injected eye on high fat diet (HFD), bottom left panel; CL5 AAV injected eye on HFD, bottom right panel.
Figure 11:
FIG. 11 illustrates retinal cryosection of NT AAV injected eye of mouse on high fat diet (HFD), top left panel; retinal cryosection of CL5 injected eye of mouse on HFD, top right panel; retinal cryosection of donor human eye, bottom left panel; retinal cryosection of donor human eye with geographic atrophy (GA)
Figure 11:
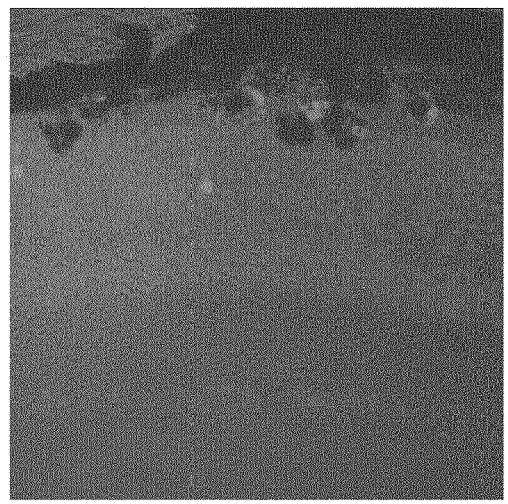
Figure 11:
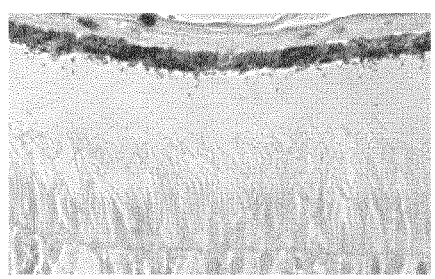
Figure 11:
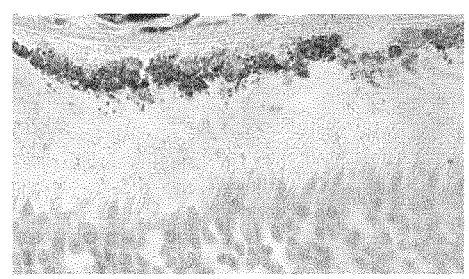

Claudin-5 Suppression and Supplementation of Mice with a High Fat Diet Induces Geographic Atrophy-Like Phenotype Given the phenotype observed with regard to enhanced fluroescein leakage at 8 PM, it was sought to induce this phenotype for a prolonged period of time using an adeno-associated virus (AAV) vector expressing claudin-5 shRNA under the control of a doxycycline inducible promoter. To this end, 10 C57BL/6 mice were injected sub-retinally with AAV-luciferase into their left eye and AAV2/9 claudin 5 into the right eye. Five mice were left on normal diet (ND) and the remaining five placed onto a high fat diet (HFD) with all mice on doxycycline water (2 mg/ml) to induce shRNA expression. Six weeks post-injection, FFA analysis showed enhanced leakage of fluorescien in the AAV2/9 claudin-5 eye compared to the AAV-luciferase injected eye (see FIG. 10). Post mortem analysis of eyes from these mice revealed a retinal pigment epithelium (RPE) phenotype similar to that observed in human subjects with GA (see FIG. 11).

Example 3

Inducible Claudin-5xTie2Cre+ Mice have a 'Leakier' Inner Blood-Retinal Barrier

Figure 12:
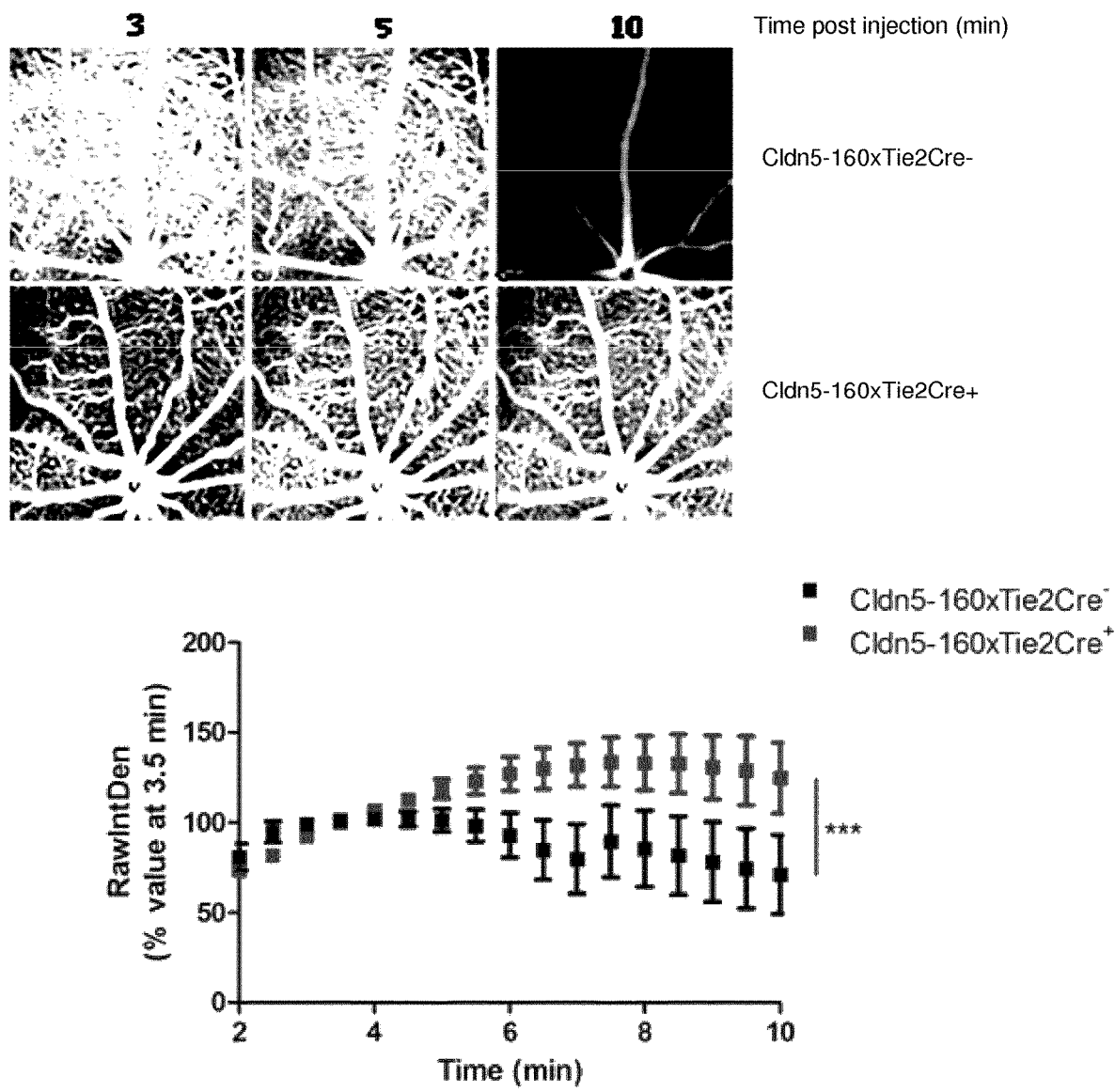
FIG. 12 illustrates inducible Claudin-5xTie2Cre mice that had their water supplemented with doxycycline to induce claudin-5 suppression for two weeks, and fundus fluorescein angiography carried out on mice that express Tie2Cre (Tie2Cre+) leading to suppressed claudin-5 levels or on Tie2Cre negative (Tie2Cre−) littermate controls in which claudin-5 levels remain unchanged, wherein equal volume/weight of sodium fluorescein was injected per mouse, and two minutes post-injection images were taken every 30 seconds up to 10 minutes with the sensitivity of the images being kept the same at each time point, and the relative image density analysed using Image J software, wherein Cldn5-160xTie2Cre+ have a more permeable retinal vasculature compared to littermate controls, and wherein representative images from one mouse of each genotype are shown at 3, 5 and 10 min post injection, and the graph below shows the average image raw intensity density for the microvasculature across all images and time points, wherein data are representative of 5 mice imaged for both genotypes and analysed by two-way ANOVA (p value ***<0.0001)

As mice that are deficient in claudin-5 are embryonic lethal, a new mouse model was generated that allows for inducible suppression of claudin-5. These mice are then crossed to the Cre-recombinase expressing (Tie2Cre) mice and animals that are Cre positive have suppressed levels of claudin-5 in their retinal endothelial cells when administered doxycycline in drinking water. Claudin-5xTie2Cre mice were administered doxycycline for two weeks and then imaged by fundus fluorescein angiography (FFA) (see FIG. 12). Inducible claudin-5xTie2Cre+ mice have more permeable retinal vessels when compared to their Tie2Cre– littermate controls.

Example 4

Figure 13:
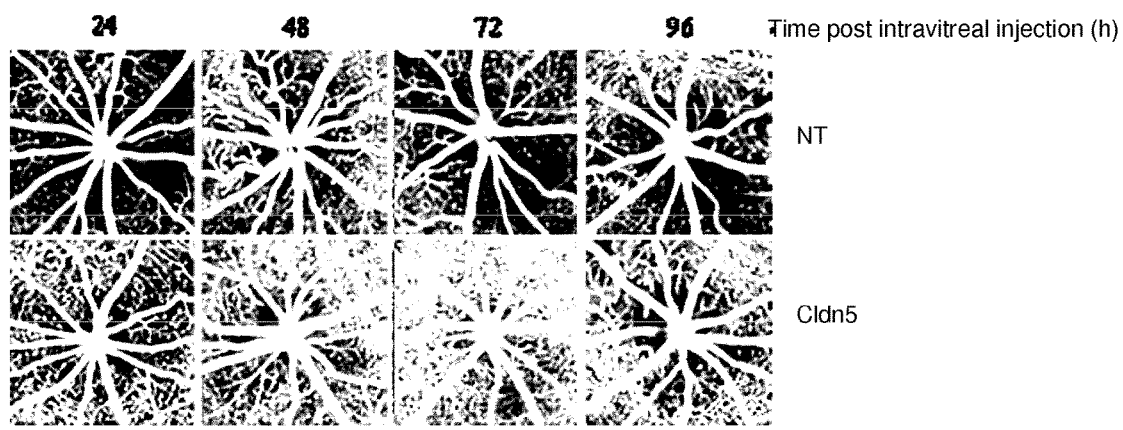
FIG. 13 illustrates C57BL/6J mice injected intravitreally with either a non-targeting (NT) or claudin-5 (Cldn5) siRNA, and fundus fluorescein angiography (FFA) carried out 24, 48, 72 and 96 hour post-injection to study inner blood-retinal barrier permeability as previously described, wherein a representative image from an individual mouse is shown from each time point and for each siRNA injected (3-4 mice were injected per siRNA group per time point)

Administration of Claudin-5 siRNA Intravitreally Leads to More Permeable Inner Retinal Blood Vessels Given suppression of claudin-5 leads to more 'leaky' vessels, it was sought to determine the time frame of when maximum suppression of claudin-5 is observed. To this end, cohorts of 3-4 mice were injected intravitreally with either a non-targeting (NT) or claudin-5 (Cldn5) siRNA and subsequently imaged 24, 48, 72 or 96 hours post-injection by FFA (see FIG. 13) prior to sacrifice for protein and transcript analysis. It appears within 24 hours mice injected with claudin-5 siRNA have more permeable retinal vessels when compared to those injected with NT siRNA.

Example 5

Tight Junction Structure Appears to Differ at 8 AM and 8 PM in C57BL/6J Mice

Figure 14:
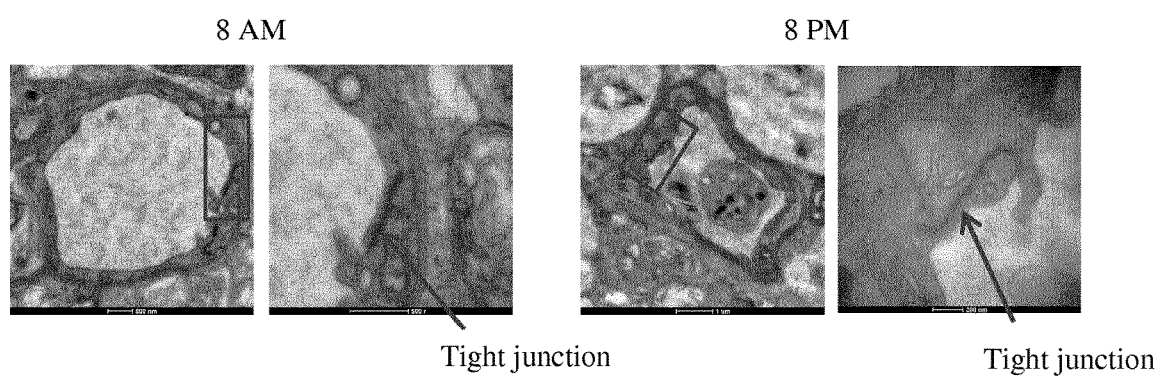
FIG. 14 illustrates C57BL/6J mice sacrificed at either 8 AM or 8 PM, wherein eyes were collected, fixed, enucleated and processed for electron microscopy analysis to look at retinal endothelial cell integrity, wherein boxes indicate regions of increased magnification, and tight junctions (as indicated by the arrow) appear to be more diffuse and less structured at 8 PM compared to 8 AM.

Previous data have shown that the inner retinal vasculature is more permeable in the evening compared to the morning by both FFA and magnetic resonance imaging (MRI). To further investigate the tight junction structure, C57BL/6J mice were sacrificed at 8 AM and 8 PM and eyes processed for electron microscopy analysis. The tight junctions at 8 AM appear more electron dense and defined when compared to 8 PM which are more diffuse and less structured in appearance (see FIG. 14).

Example 6

Figure 15:
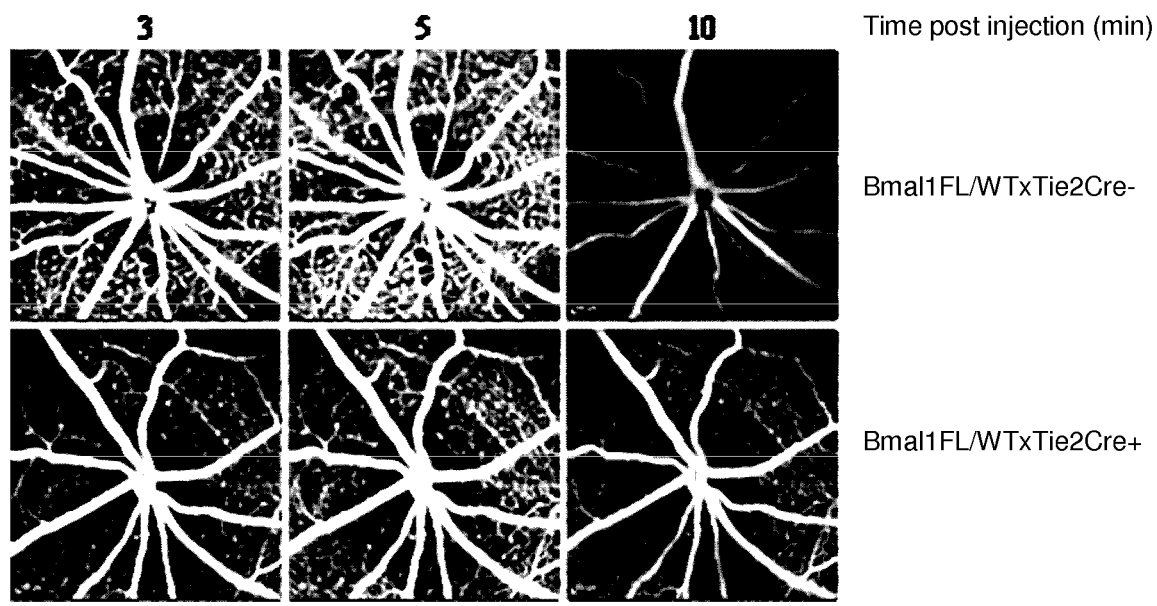
FIG. 15 illustrates Bmal1FL/WTxTie2Cre mice placed on a high fat diet (HFD) for 1 week and then imaged by fundus fluorescein angiography to study retinal vasculature permeability as previously described, wherein mice that are Tie2Cre+ lack one copy of Bmal1 in their retinal endothelial cells, and Bmal1FL/WTxTie2Cre+ mice on HFD have a more permeable retinal vasculature when compared to their littermate Tie2Cre− controls, wherein a representative image is shown from 3, 5 and 10 min post-injection for both Bmal1FL/WTxTie2Cre+ and Bmal1FL/WTxTie2Cre− mice on HFD, and the graph below shows the relative image density for the microvasculature for both genotypes across all time points, which was analysed using Image J software, and wherein data are representative of 6-8 mice imaged for both genotypes and analysed by two-way ANOVA (p value *0.04).
Figure 15:
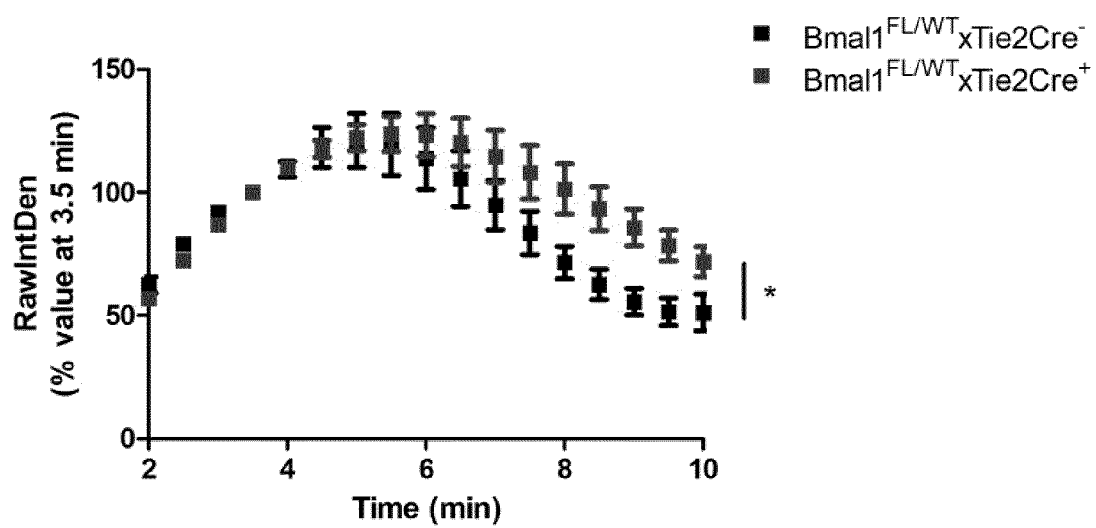

Supplementation of Bmal1xTie2Cre Mice with a High Fat Diet Induces 'Leakier' Inner Blood-Retinal Vessels Given the phenotype observed with no change in enhanced fluorescein leakage at 8 PM with Bmal1xTie2Cre+ mice as seen in C57BL/6J mice, it was sought to see if supplementation of a high fat diet (HFD) could induce enhanced fluorescein leakage. After one week of the mice being on HFD, FFA was carried out to study retinal vessel integrity. Bmal1xTie2Cre+ mice lack one copy of the clock gene Bmal1 in their endothelial cells. Bmal1xTie2Cre+ mice on HFD have more permeable retinal vessels when compared to their littermate Bmal1xTie2Cre– controls (see FIG. 15).

Together, these findings suggest claudin-5 and components of the circadian clock are direct targets for therapeutic intervention in GA, as persistent suppression of claudin-5 induces a GA phenotype, therefore regulating its levels can prevent the phenotype.

The invention claimed is:

1. A method for the treatment of age-related macular degeneration in a subject, the method comprising the step of increasing or decreasing the amount of an inner-blood-retinal-barrier (iBRB) protein and a circadian clock protein in the subject, wherein the iBRB protein is a claudin-5 protein, and wherein the circadian clock protein is selected from period-1 (Per-1), period-2 (Per-2), period-3 (Per-3), cryptochrome-1 (Cry-1), cryptochrome-2 (Cry-2), Clock, brain and muscle aryl hydrocarbon receptor nuclear translocator like-1 (BMAL-1), brain and muscle aryl hydrocarbon receptor nuclear translocator like-2 (BMAL-2), Rev-ErbA alpha (NR1 D1), and combinations each thereof.

2. The method according to claim 1, wherein the method comprises increasing the amount of the inner-blood-retinal-barrier (iBRB) protein over a period of 24 hours.

3. The method according to claim 1, wherein the method comprises decreasing the amount of the inner-blood-retinal-barrier (iBRB) protein over a period of 24 hours.

4. The method according to claim 1, wherein the method comprises sequentially increasing and decreasing the amount of the inner-blood-retinal-barrier (iBRB) protein over a period of 24 hours.

5. The method according to claim 1, wherein the method comprises increasing the amount of the circadian clock protein over a period of 24 hours.

6. The method according to claim 1, wherein the method comprises decreasing the amount of the circadian clock protein over a period of 24 hours.

7. The method according to claim 1, wherein the method comprises sequentially increasing and decreasing the amount of the circadian clock protein over a period of 24 hours.

8. The method according to claim 1, wherein the method comprises sequentially increasing the amount of the inner-blood-retinal-barrier (iBRB) protein over a first period of 12 hours; and decreasing the amount of the inner-blood-retinal-barrier (iBRB) protein over a second period of 12 hours.

9. The method according to claim 1, wherein the method comprises sequentially increasing the amount of the circadian clock protein over a first period of 12 hours; and decreasing the amount of the circadian clock protein over a second period of 12 hours.

10. The method according to claim 1, wherein the method comprises increasing or decreasing the amount of the inner-blood-retinal-barrier (iBRB) protein and the circadian clock protein, each relative to a normal control, wherein a normal control is an amount of the inner-blood-retinal-barrier (iBRB) protein and the circadian clock protein in a healthy subject.

11. The method according to claim 10, wherein the method comprises increasing or decreasing the amount of the inner-blood-retinal-barrier (iBRB) protein and the circadian clock protein; each by up to 50% relative to the normal control.

12. The method according to claim 10, wherein the method comprises increasing or decreasing the amount of the inner-blood-retinal-barrier (iBRB) protein and the circadian clock protein; each by more than 50% relative to the normal control.

13. The method according to claim 1, wherein the age-related macular degeneration is dry-AMD.

14. The method according to claim 1, wherein the age-related macular degeneration is geographic atrophy (GA).

15. The method according to claim 1, wherein the circadian clock protein is brain and muscle aryl hydrocarbon receptor nuclear translocator like-1 (BMAL-1).

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Unknown
<220> FEATURE:
<223> OTHER INFORMATION: Synthetic primer sequence

<400> SEQUENCE: 1
tttcttctat gcgcagttgg                                              20
```

```
<210> SEQ ID NO 2
<211> LENGTH: 20
<212> TYPE: DNA
<213> ORGANISM: Unknown
<220> FEATURE:
<223> OTHER INFORMATION: Synthetic primer sequence

<400> SEQUENCE: 2
gcagtttggt gcctacttca                                              20

<210> SEQ ID NO 3
<211> LENGTH: 25
<212> TYPE: DNA
<213> ORGANISM: Unknown
<220> FEATURE:
<223> OTHER INFORMATION: Synthetic primer sequence

<400> SEQUENCE: 3
tcacccacac tgtgcccatc tacga                                        25

<210> SEQ ID NO 4
<211> LENGTH: 25
<212> TYPE: DNA
<213> ORGANISM: Unknown
<220> FEATURE:
<223> OTHER INFORMATION: Synthetic primer sequence

<400> SEQUENCE: 4
cagcggaacc gctcattgcc aatgg                                        25
```